Figure 1:
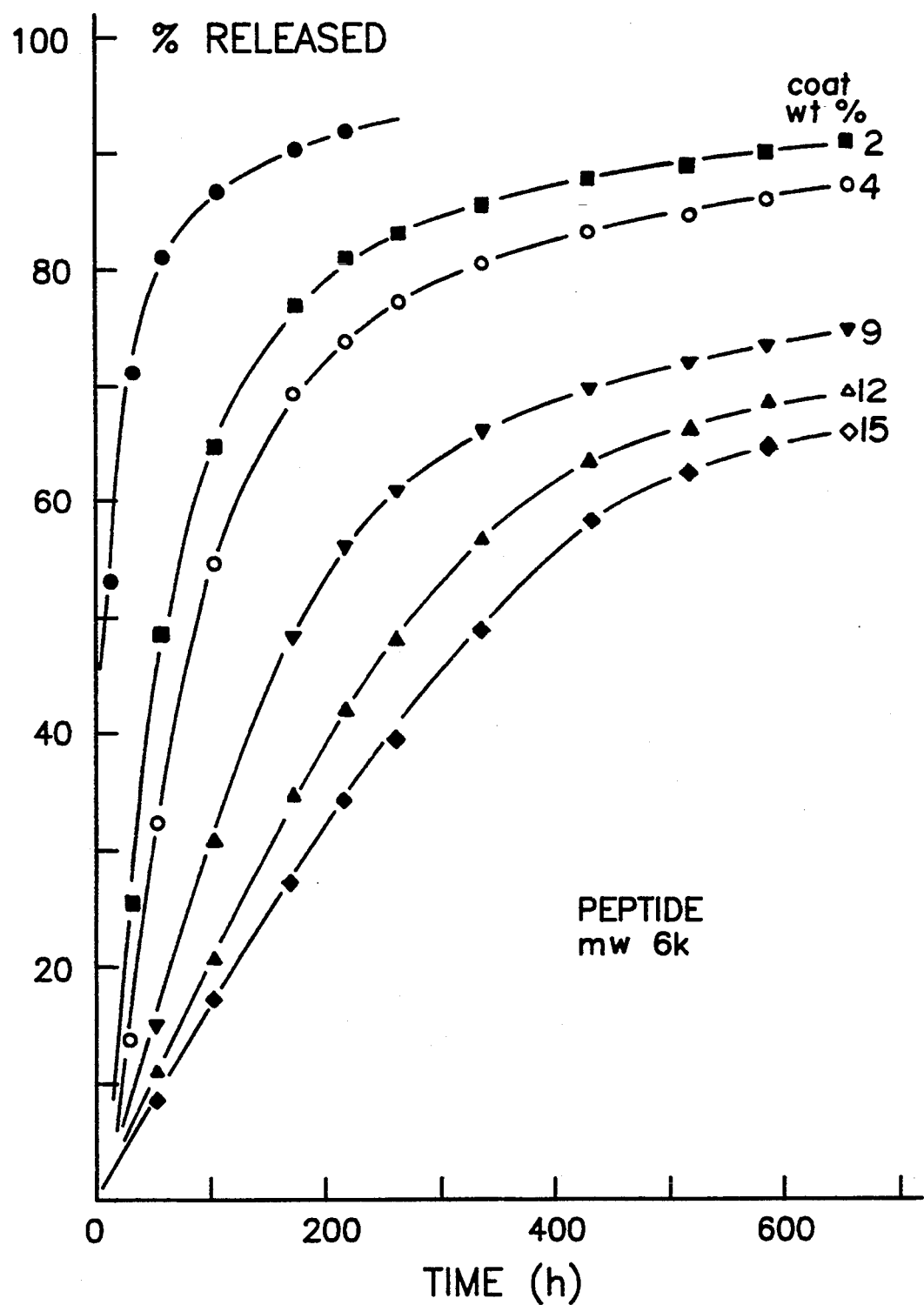

United States Patent [19]

Williams et al.

[11] Patent Number: 5,342,622
[45] Date of Patent: Aug. 30, 1994

[54] SUBDERMAL BIOCOMPATIBLE IMPLANTS

[75] Inventors: Alan H. Williams, Mount Duneed Via Belmont; Linton D. Staples, East Kew; William J. Thiel, Brighton; Richard C. Oppenheim, Kew; Iain J. Clarke, Malvern East, all of Australia

[73] Assignees: The State of Victoria; Victorian College of Pharmacy Ltd.; Monash Medical Centre, Victoria, Australia

[21] Appl. No.: 605,158

[22] Filed: Oct. 31, 1990

Related U.S. Application Data

[63] Continuation of Ser. No. 166,962, Mar. 30, 1988, abandoned.

[30] Foreign Application Priority Data

May 16, 1986 [AU] Australia ............... PH 05932/86
May 16, 1986 [AU] Australia ............... PH 05933/86

[51] Int. Cl.$^5$ ............... A61F 2/02; A61K 9/28; A61K 9/32; A61K 9/14
[52] U.S. Cl. ............... 424/425; 424/423; 424/424; 424/474; 424/482; 424/489
[58] Field of Search ............... 424/462, 424, 422, 423, 424/474, 482, 425, 489

[56] References Cited

U.S. PATENT DOCUMENTS

| | | | |
|---|---|---|---|
| 3,830,907 | 8/1974 | Short et al. | 424/19 |
| 4,539,199 | 9/1985 | Orbán et al. | 424/462 X |
| 4,666,704 | 5/1987 | Shalati et al. | 424/19 |
| 4,765,980 | 8/1988 | Deprince et al. | 424/608 |
| 4,784,858 | 11/1988 | Ventouras | 424/473 X |

OTHER PUBLICATIONS

"Coating of Tablets and Small Particles with Acrylic Resins by Fluid Bed Technology", *International Journal of Pharmaceutical Technology & Product Manufacture*, vol. 2, No. 4, Dec. 1981, pp. 31–42.

*Primary Examiner*—Thurman K. Page
*Assistant Examiner*—C. Azpuru
*Attorney, Agent, or Firm*—Bacon & Thomas

[57] ABSTRACT

The present invention provides pharmaceutical or veterinary implants which, when subdermally administered releases a peptide or protein in a substantially continuous manner. The implant includes the peptide or protein and an excipient encased within a polymeric coating which is permeable, swellable and, at normal physiological pH, is non-rupturing, non-dissolving and does not degrade over the useful life the implant. The coating forms a release rate limiting barrier. All of the components used to make the implant are of a biocompatible nature. The implant is particularly useful for the sustained release of proteins or peptides for regulating the hormonally controlled reproductive cycle in sheep.

15 Claims, 7 Drawing Sheets

SUBDERMAL BIOCOMPATIBLE IMPLANTS

This application is a continuation of application Ser. No. 07/166,962, filed Mar. 30, 1988, now abandoned.

This invention relates to biocompatible implants which can be administered parenterally, for human or veterinary applications.

More particularly, the invention is concerned with biocompatible implants for the administration of peptides or proteins, including hormones, to animals including man, which provide substantially continuous and uniform release of such peptides or proteins over an extended period. "Biocompatible" in the present specification means that all components of the implant should be physiologically tolerable and should not cause an adverse histological response when implanted. Implants are solid devices suitable for parenteral delivery and may be in a range of sizes for example, from less than 1 mm diameter to several cm, although most commonly they are a few mm in diameter.

One application of the present invention is in the provision of methods and means for inducing ovulation during anoestrus in seasonally breeding animals, especially sheep. This aspect of the invention is particularly concerned with the administration of ovulation-regulating hormones to such animals by means of biocompatible implants which can be administered subcutaneously.

In certain areas of Australia, prime lamb producers prefer to join their flocks in springtime. Border Leicester×Merino ewes joined at this time exhibit variable onset of breeding activity between years and within a year. This can result in considerable uncertainty about both the number of ewes that will lamb and when lambs will arrive and will often result in an extended lambing. A widely spread lambing period can be difficult to manage, interferes with other farm operations and often results in feed being wasted on ewes which are several weeks off lambing.

There is, accordingly, a need for a cheap and effective technique for hormonally inducing ovulation and fertile oestrus. Using such a technique, the producer would be able to reliably obtain fertile matings in the anoestrus season. Advantage could then be taken of better management of the lamb flock because of a more compact lambing and also of the higher prices obtained for early finished lambs.

The release from the pituitary gland of luteinizing hormone (LH) is controlled by pulsatile discharges of gonadotrophin-releasing hormone (GnRH) from the median eminence of the hypothalamus. GnRH is also known as gonadotrophin releasing factor, luteinizing hormone releasing factor, luteinizing hormone releasing hormone and lulibern, and has the following amino acid sequence:

pyroGlu—His—Trp—Ser—Tyr—Gly—Leu—Arg—Pro—Gly·

As a result of GnRH secretion, pulsatile secretory discharges of LH from the pituitary gland cause transitory elevations of LH in peripheral blood (pulses). The frequency of these pulses is relatively lower during the luteal phase of the sheep oestrous cycle than during the follicular phase. During the anoestrus ("non-breeding") season for sheep the frequency of LH pulses is lower than at any other time. Predominant endocrine events that occur in the preovulatory period are increases in the pulsatile frequency of LH secretion and a rising peripheral plasma concentration of oestrogen. Such events are triggered by the regression of the corpus luteum leading to a fall in plasma progesterone levels. Increased LH and oestrogen secretion in the follicular phase lead to a massive release of LH (the preovulatory LH surge) that causes ovulation.

During anoestrus the LH pulse frequency remains low due to a seasonal alteration in the feedback effects of oestrogen on the hypothalamus-pituitary unit. Thus, at this time, there are no cyclic increases in LH and oestrogen secretion or preovulatory LH surges, consequently ovulation does not occur.

By treating anoestrous ewes with repeated pulses of GnRH or LH it is possible to induce a preovulatory LH surge and cause ovulation. Furthermore, although the GnRH/LH system is generally characterised by pulsatile secretory patterns, it is possible to promote LH surges and cause ovulation in anoestrous ewes by the infusion of low doses (up to 250 ng/h) of GnRH in a constant rather than a pulsatile mode. If this procedure is preceded by a period of progesterone treatment, then a large proportion of the treated ewes will show behavioural oestrus and can become pregnant if mated.

One major attraction of this method for the induction of fertile oestrus in anoestrous ewes is that the treatment phase is short and animals are mated within a week of GnRH treatment. With current technology the major problem that prevents commercial development is the method of delivery of GnRH. This can be achieved by the use of osmotic mini-pumps (Alzet; Alza Corporation), but these are too costly for on-farm use and require surgical subcutaneous insertion and recovery.

There is clearly a need, therefore, for a relatively inexpensive and efficient biocompatible delivery system which will release GnRH at a suitable rate over a sufficient period of time to induce ovulation in anoestrous ewes in conjunction with a progesterone/progestagen pre-treatment.

It has long been appreciated that the continuous release of certain drugs over an extended period following a single administration could have significant practical advantages in clinical or veterinary practice, and compositions have already been developed to provide extended release of a number of useful drugs, after oral dosing (see, for example, Remington's Pharmaceutical Sciences, published by, Mack Publishing Company, Easton, Pa., U.S.A., 15th Edition, 1975, pages 1618-1631), after parenteral administration (ibidem, pages 1631-1643), and after topical administration (see, for example, United Kingdom Patent Number 1,351,409).

A suitable method of parenteral administration is sub-dermal injection or implantation of a solid body, for example a pellet or a film, containing the drug, and a variety of such implantable devices has been described. In particular, it is known that, for many drugs, suitable implantable devices for providing extended drug release may be obtained by encapsulating the drug in a suitable polymer, or by dispersing the drug in a matrix of such a polymer.

Suitable polymers for use in sustained release formulations are well known, and include polyesters which gradually become degraded by hydrolysis when placed in an aqueous, physiological-type environment. Particular polyesters which have been used are those derived from hydroxycarboxylic acids, and much prior art has been directed to polymers derived from alpha-hydroxycarboxylic acids, especially lactic acid in both its racemic and optically active forms, and glycolic acid, and copolymers thereof—see, for example, U.S. Pat. Nos. 3,773,919 and 3,887,699; Jackanicz et al., Contraception, 1973, 8, 227–234; Anderson et al., ibidem, 1976, 11, 375–384; Wise et al., Life Sciences, 1976,19, 867–874; Woodland et al., Journal of Medicinal Chemistry, 1973, 16, 897–901; Yolles et al., Bulletin of the Parenteral Drug Association, 1976, 30, 306–312; Wise et al., Journal of Pharmacy and Pharmacology, 1978, 30, 686–689 and 1979, 31, 201–204.

Australian Patent Specification No. 79986/82 describes continuous release compositions, including implants, which consist of a polylactide and an acid stable polypeptide hormone. The specification describes how it is possible to provide continuous release of the polypeptide from the implant in vivo by selection of the appropriate molecular weight of the polylactide.

In general, the implants described in the said application often manifest a so-called "dead phase" following administration, that is, a period during which essentially none of the active polypeptide ingredient is released. Continuous release occurs only after the expiration of the dead phase, which usually extends over several days.

A further problem which may be associated with the prior art implant compositions is "dumping", that is the early and relatively abrupt release of a substantial proportion of the active agent over a relatively short period, followed by slower, more uniform release over the remaining lifetime of the implant.

Another approach is to use the so-called "mini-osmotic pump" maintained above, but although these devices can provide satisfactory controlled-release characteristics, they are comparatively expensive. They are also non-biodegradable and require surgical implantation and removal.

The present invention seeks to provide a biocompatible implant which will provide for the continuous release of peptides or proteins, including hormones, over a desired period, at a substantially constant rate, and without any significant dead phase or dumping.

We have now found that implants which satisfy the above requirements, at least in part, can be prepared using readily available materials and techniques already used in the known prior art relating to tabletting.

According to the present invention there is provided a pharmaceutical or veterinary implant which, when parenterally administered releases a peptide or protein in a substantially continuous manner, characterised in that the implant comprises the peptide or protein and an excipient encased within a polymeric coating which is permeable, swellable9 and which at normal physiological pH is non-rupturing, non-dissolving and does not degrade over the useful life of the implant, said coating forming a release rate limiting barrier, and wherein all of the implant components are of a biocompatible nature.

The excipient may be a water-soluble or water-insoluble material or a mixture of water-soluble and water-insoluble materials.

One of the functions of the water-insoluble excipient, if used, is to control the dissolution of the other materials within the implant, i.e. the protein or peptide and the water-soluble excipient, if used. This is believed to result from the water-insoluble material inhibiting absorption of water by, and dissolution of, the soluble components, thereby affecting the rate of dissolution. The preferred excipient is calcium phosphate, but those skilled in tabletting art will appreciate that other suitable excipients may be used. By varying the types and relative proportions of excipients the release rate of particular peptides or proteins may be varied.

In a preferred form the permeable coating is essentially neutral. By describing the polymeric coating as essentially neutral we mean than ionisable groups are absent from the polymer chains. Thus our description would admit of the presence of normal initiator residues and surfactants conventionally used to prepare the polymer dispersions via emulsion polymerisation. We believe the essentially neutral property of the coating aids the permeation of peptides and proteins which have ionisable groups present.

"Permeable" means that water (or physiological liquids) as well as the protein or peptide may pass through the coating. The function of the permeable coating material is to form a release rate limiting barrier around the protein or peptide. By selecting a material of the appropriate permeability, the rate of ingress of water or physiological liquid into the matrix and of egress out of the matrix of the aqueous solution formed therein can be controlled; hence controlling the rate of release of the protein or peptide from the matrix. A particularly, preferred coating material is a neutral copolymer based on poly(meth)acrylic acid esters. Addition polymers are preferred polymers for the coating.

One particularly suitable coating material is "Eudragit E30D", (Rohm Pharma GmbH), an aqueous film forming dispersion of a copolymer of ethyl acrylate and methyl methacrylate. This coating is swellable. Coatings prepared from aqueous dispersion of film forming polymer particles are preferred. The permeability of the coating can be varied by the thickness of the coating as well as by the inclusion of water soluble materials such as polyethylene glycol or by the inclusion of mineral extender particles such as clay. Preferably the thickness of the coating is 3–60 μm which for 2.5 mm implants corresponds to a coating of about 1 to 20 weight per cent of the implant. We believe that the permeability of the coating may also be varied by the coating being swellable and in a preferred embodiment the coating should be swellable.

By "swellable" we mean that the volume of the coating increases when placed in contact with physiological liquids.

Once formed, the implants of the invention may be placed in the body of an animal which it is desired to treat, by any suitable known technique, for example, intramuscular or subcutaneous injection, or by subdermal surgical implantation using conventional clinical or veterinary techniques.

As indicated above, a specific application of the invention which is of particular interest is the administration to sheep of the peptide hormone GnRH. However, the invention is not limited to this particular application and may be used for any suitable peptide or protein, the main requirement being that the active ingredient must be able to diffuse or be transported through the coating layer on the implant. Generally, peptides or proteins having a molecular weight up to about 50,000 Daltons, more particularly 1000 to 30,000 Daltons, will be suitable. By way of example, apart from GnRH, epidermal growth factor (EGF), luteinizing hormone (LH) and growth hormone (GH) have all been successfully incorporated into, and shown to be released from, implants in accordance with the invention. Prolactin is another suitable peptide.

The invention will be further described and illustrated by reference to the following examples. (All parts and proportions are by weight.)

Figure 2:
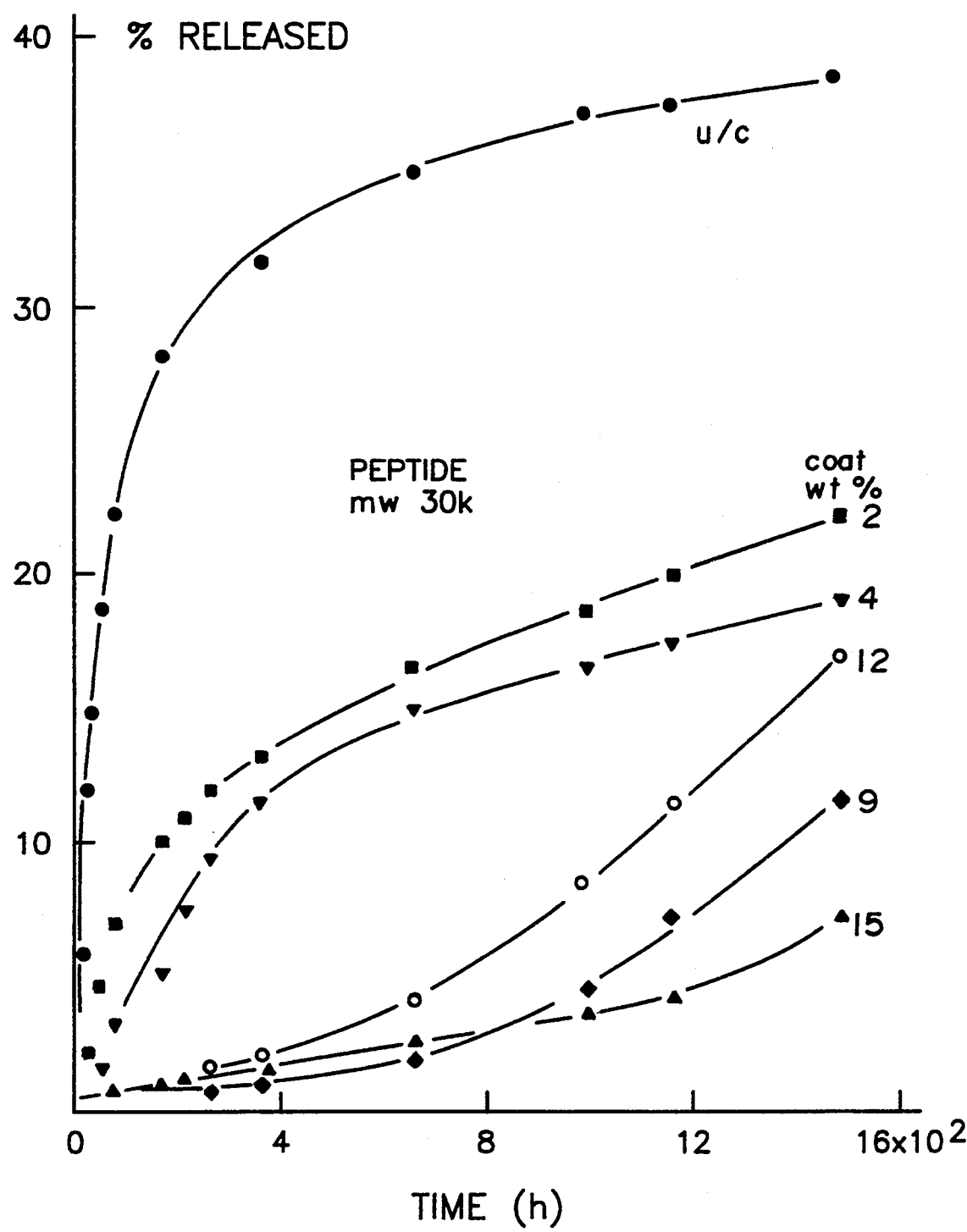
Figure 3:
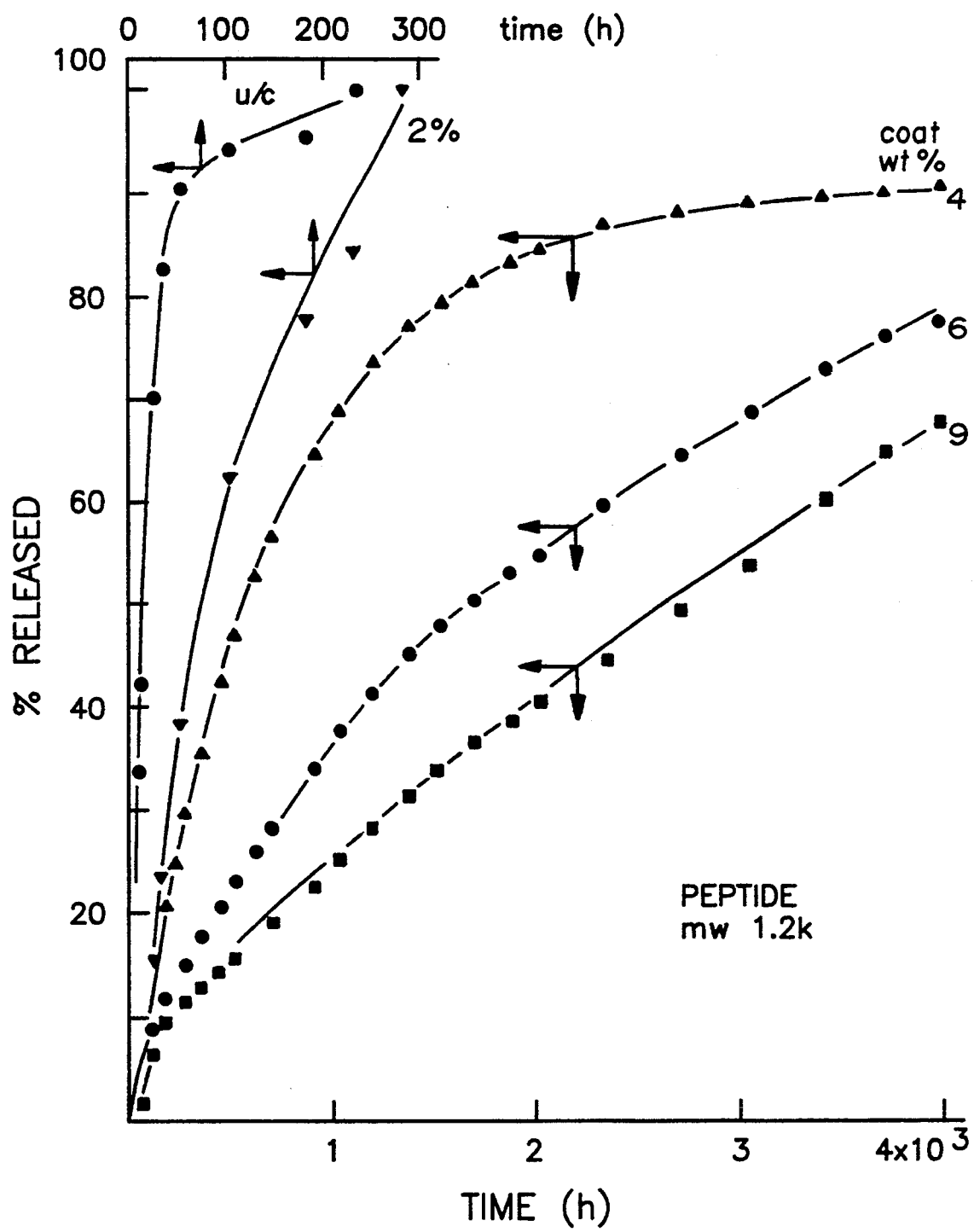
Figure 4:
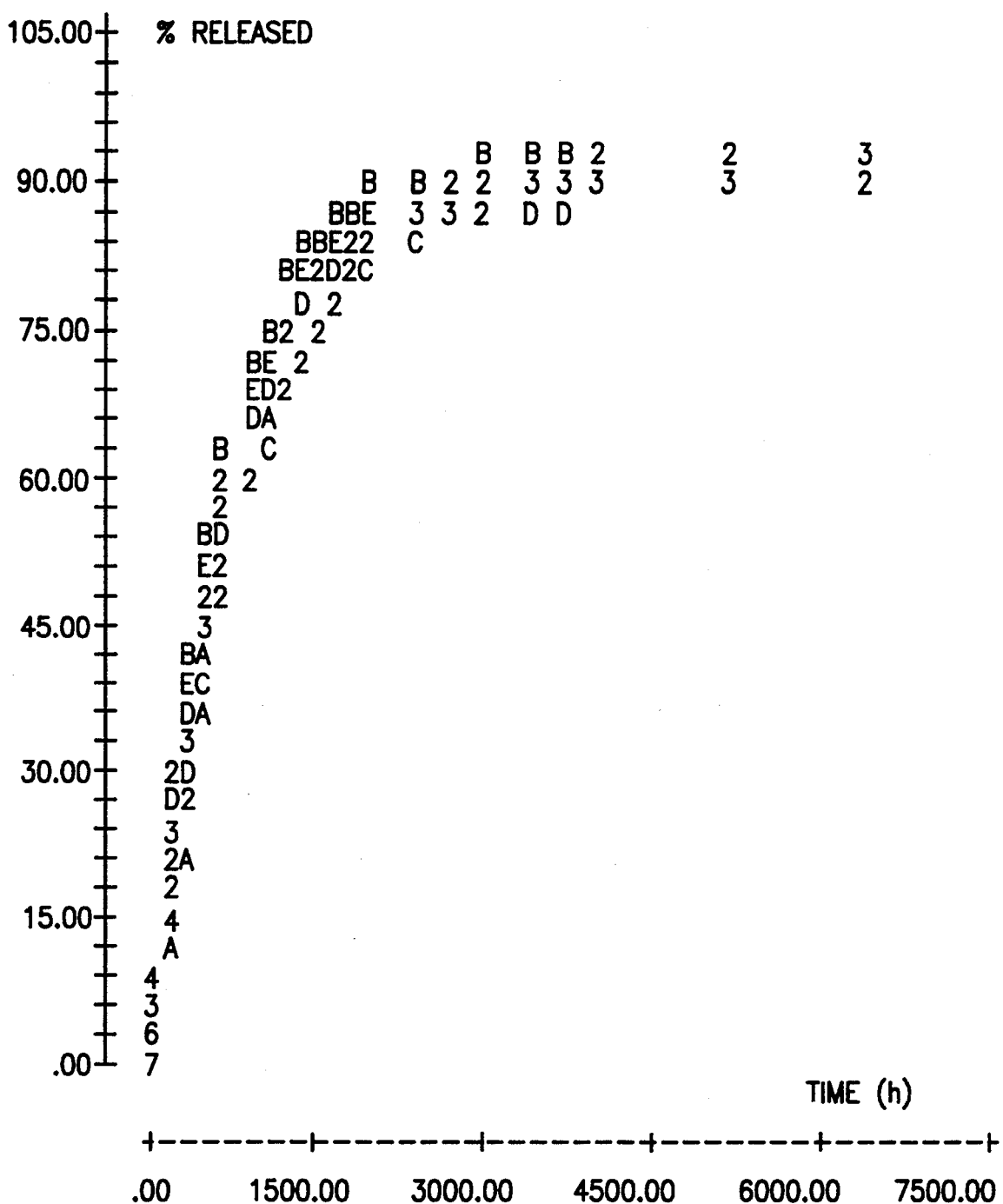
Figure 5:
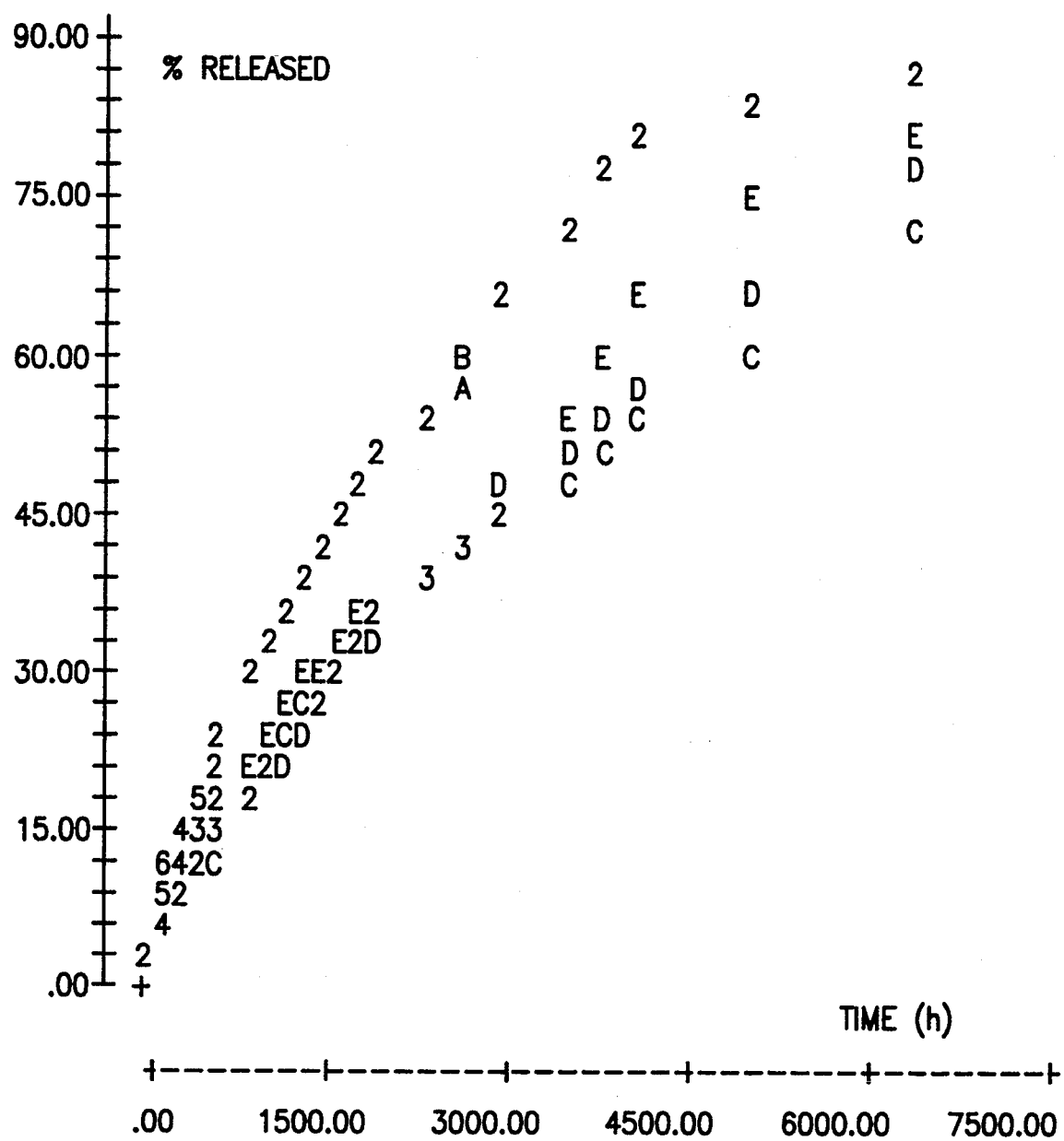
Figure 6:
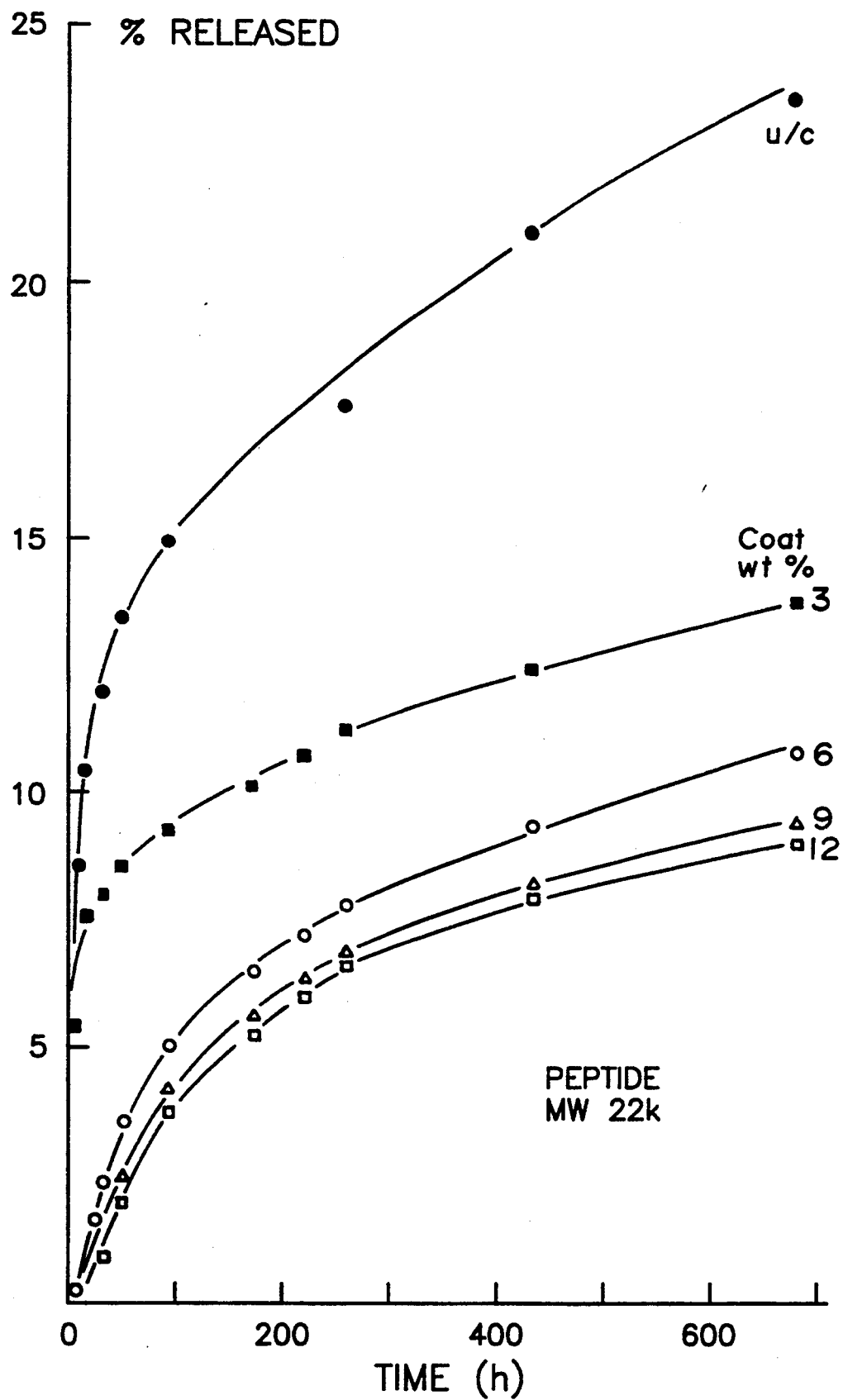
Figure 7:
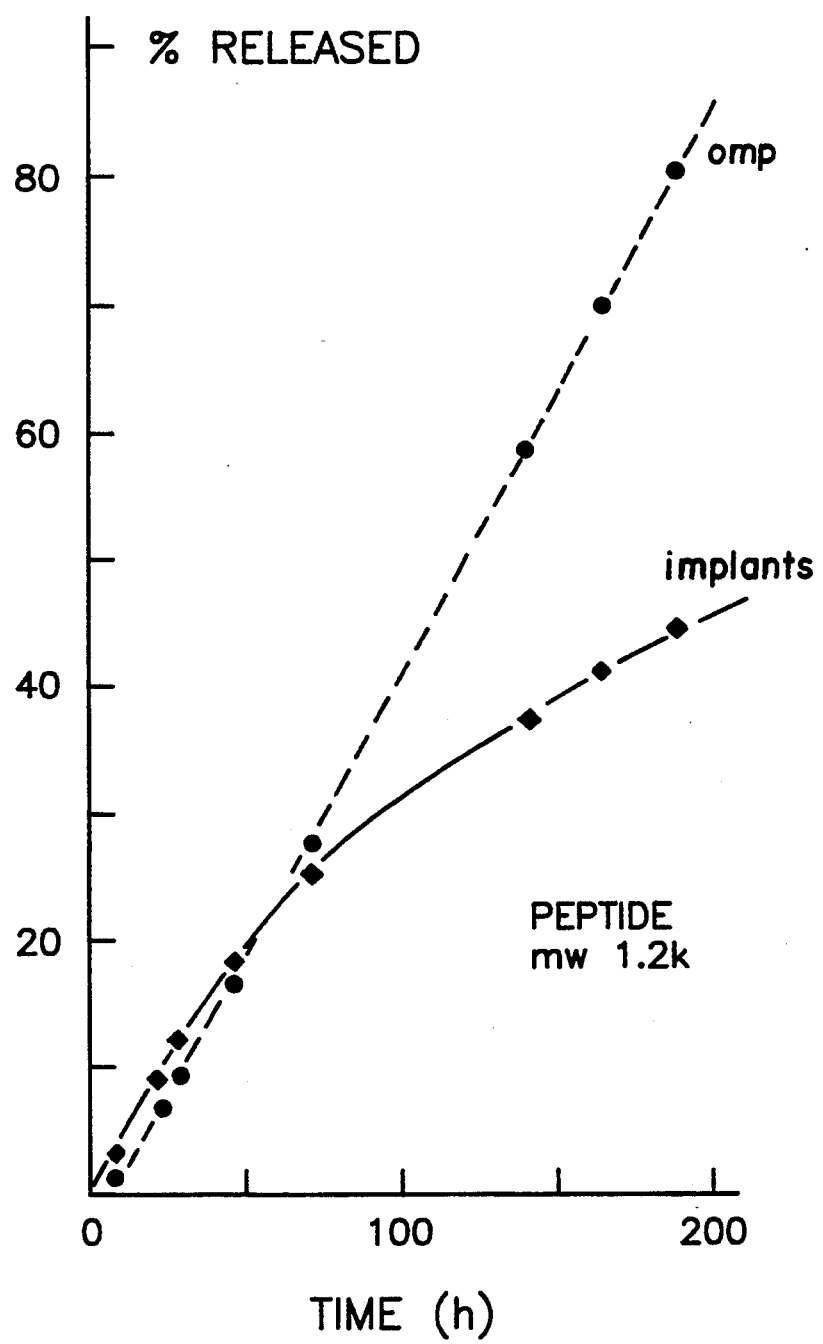

Reference will be made to the accompanying drawings in which:

FIGS. 1 to 3 are graphs showing the rate of in vitro release of respectively EGF, LH and GnRH from uncoated implants and coated implants in accordance with this invention;

FIGS. 4 and 5 are graphs showing the rate of in vitro release of GnRH from batches of five individual implants having respectively 4% and 9% coatings in accordance with this invention;

FIG. 6 is a graph showing the rate of in vitro release of HGH from uncoated implants and implants coated in accordance with this invention; and FIG. 7 is a graph which compares the in vitro release of GnRH from osmotic mini-pumps and implants in accordance with this invention.

EXAMPLE 1

General Method for Preparation of Implants

The water-insoluble excipient (e.g., calcium phosphate) is thoroughly mixed with the protein or peptide in an amount sufficient to give the required dosage unit in the final product. Usually, the protein or peptide will be in the form of a solution or dispersion to facilitate mixing.

The water-soluble excipient (e.g., lactose), if used, is then added, together with other desired additives, e.g. a lubricating agent such as magnesium stearate, and mixed in to form a dry powder. The powder is then compressed into tablet-shaped "cores" of the desired size and shape.

The compressed cores are then coated in a pan coater by spraying with a solution or dispersion of the coating material in an amount sufficient to give implants having the required coating thickness. Typically the implants will weigh about 30 mg and be about 2.5 mm in diameter.

EXAMPLE 2

Implants Containing Radio-iodinated EGF

Using the general method of Example 1, implant cores were prepared based on the following formulation.

| | | |
|---|---|---|
| 98% | Calcium phosphate | (76%) |
| | Lactose | (24%) |
| 2% | Magnesium stearate | |

The prepared implants had an average weight of 31 mg and contained 4.96 μg of EGF and 0.2 μCi of $I^{125}$-EGF. They were coated with Eudragit E30D in amounts of 0, 2, 4, 9, 12 and 15% (by weight).

Release rates were determined by placing the implants in 1 ml of foetal calf serum 10% in RPMI1640. At various times all the liquid was drawn off and counted to determine the quantity of $I^{125}$-EGF which had been released. One milliliter of fresh liquid was replaced after sampling. The results are shown in Table 1 and FIG. 1 as the cumulative percentage of EGF released at different times, for implants with various coating thicknesses (expressed as weight % of implant).

TABLE 1

In vitro release of EGF over 28 days.
The % release is the mean value from 5 implants

| Uncoated | |
|---|---|
| Time (h) | Release (%) |
| 2 | 36.9 |
| 4 | 47.1 |
| 6 | 53.4 |
| 22 | 71.7 |
| 48 | 81.2 |
| 96 | 87.1 |
| 168 | 90.9 |
| 216 | 92.7 |

| Time (h) | % release from implants with various coatings | | | | |
|---|---|---|---|---|---|
| | 2% coat | 4% | 9% | 12% | 15% |
| 6 | 6.2 | 3.4 | 0.7 | 0.3 | 0.1 |
| 22 | 25.7 | 13.2 | 5.8 | 3.3 | 2.0 |
| 48 | 48.8 | 32.7 | 14.5 | 10.3 | 8.0 |
| 96 | 65.5 | 54.7 | 30.5 | 20.8 | 17.4 |
| 168 | 76.8 | 69.0 | 48.2 | 34.6 | 27.8 |
| 216 | 81.0 | 74.2 | 56.3 | 41.9 | 34.3 |
| 264 | 83.5 | 77.3 | 61.2 | 47.8 | 39.2 |
| 336 | 85.6 | 80.3 | 65.8 | 56.4 | 48.6 |
| 432 | 88.1 | 83.2 | 69.4 | 62.8 | 57.8 |
| 528 | 89.2 | 84.9 | 71.5 | 65.7 | 61.6 |
| 600 | 90.5 | 86.6 | 73.6 | 68.0 | 64.3 |
| 672 | 91.2 | 87.6 | 74.8 | 69.3 | 66.0 |

EXAMPLE 3

Implants Containing Radio-iodinated LH; In Vitro Release

The release of LH from individual implants was determined at various levels of coating. Using a similar method to that of Example 2, the amount of LH was determined by RIA techniques. The percentage of LH released is tabulated (Table 2) and shown in FIG. 2. The results show that uncoated implants released LH at the greatest rate and that the rate of release can be controlled by varying the coating thickness.

TABLE 2

In vitro release of LH over 63 days.
The % release is from individual implants

| Time (h) | % release from an implant with various coatings | | | | | |
|---|---|---|---|---|---|---|
| | Uncoated | 2% coat | 4% | 9% | 12% | 15% |
| 2 | 2.5 | | | | | |
| 4 | 4.3 | | | | | |
| 6 | 5.8 | 0.1 | 0 | 0 | 0 | 0 |
| 22 | 11.9 | 1.1 | 0.5 | 0 | 0 | 0 |
| 30 | 14.8 | 1.9 | 0.7 | 0 | 0 | 0 |
| 48 | 18.7 | 3.5 | 1.3 | 0.2 | 0.3 | 0.2 |
| 73 | 22.3 | 6.8 | 3.0 | 0.4 | 0.8 | 0.4 |
| 168 | 28.4 | 9.9 | 4.9 | 0.7 | 1.3 | 0.8 |
| 214 | | 10.8 | 7.3 | 0.8 | 1.4 | 1.0 |
| 262 | | 11.9 | 9.3 | 0.8 | 1.5 | 1.1 |
| 362 | 31.9 | 13.2 | 11.5 | 0.9 | 1.9 | 1.3 |
| 676 | 35.4 | 16.4 | 14.9 | 1.7 | 4.0 | 2.5 |
| 1014 | 37.5 | 18.6 | 16.4 | 4.4 | 8.3 | 3.6 |
| 1180 | 37.9 | 20.0 | 17.4 | 7.0 | 11.3 | 4.0 |
| 1516 | 38.9 | 22.2 | 19.0 | 11.4 | 16.8 | 7.0 |

EXAMPLE 4

Implants Containing Radio-iodinated GnRH; In Vitro Release

The release of $1^{125}$-GnRH was determined from uncoated and coated implants with varying coat thickness. The percentage of GnRH released was averaged for 5 implants and is tabulated (Table 3) and plotted in FIG. 3. The results show that the rate of release is retarded by the coating and, by varying the thickness of the coating, can be controlled over a wide range and for periods up to 4–10 months.

Samples of the released GnRH were subjected to analysis to determine the amount of free $I^{125}$. In all samples taken free iodine accounted for less than 8% of the activity, indicating the radiolabelled peptide was intact. FIG. 3 shows the mean release. There were considerable variation in the release rate; FIGS. 4 and 5 show the results from 5 individual implants with 4 and 9% coating; the general trend shown was that the rate of release became more variable as the amount of coating increased.

TABLE 3

In vitro release of GnRH over 298 days.
The % release is the mean value for 5 implants.

| Time (h) | % released from implant | |
|---|---|---|
| | Uncoated | 2% Coat |
| 2 | 21.4 | — |
| 4 | 34.1 | — |
| 6 | 42.2 | 2.1 |
| 22 | 70.4 | 16.0 |
| 30 | 82.9 | 23.7 |
| 48 | 90.5 | 38.4 |
| 97 | 94.2 | 62.3 |
| 168 | 95.9 | 78.4 |
| 218 | 100.4 | 84.7 |
| 265 | — | 101.6 |

| Time (h) | % release from implants | | |
|---|---|---|---|
| | 4% coat | 6% | 9% |
| 6 | 0 | 0 | 0 |
| 22 | 1.7 | 0.4 | 0.1 |
| 30 | 3.9 | 1.3 | 0.2 |
| 48 | 7.9 | 4.4 | 1.6 |
| 97 | 14.4 | 9.3 | 6.5 |
| 168 | 21.0 | 12.3 | 9.8 |
| 218 | 25.5 | 13.9 | 11.2 |
| 265 | 29.9 | 15.6 | 12.2 |
| 336 | 35.5 | 17.8 | 13.3 |
| 600 | 52.9 | 26.4 | 17.8 |
| 886 | 64.9 | 34.2 | 23.2 |
| 1009 | 69.1 | 37.5 | 25.6 |
| 1367 | 77.2 | 45.2 | 31.9 |
| 1686 | 81.7 | 50.7 | 36.8 |
| 2018 | 84.7 | 55.2 | 40.9 |
| 2711 | 88.4 | 64.4 | 49.3 |
| 3414 | 89.8 | 72.9 | 60.0 |
| 4032 | 90.6 | 77.7 | 67.7 |
| 5062 | 91.3 | 81.7 | 74.0 |
| 6407 | 92.0 | 85.3 | 80.4 |

EXAMPLE 5

In vitro Release of Radio-iodinated Human Growth Hormone (HGH)

The release of $I^{125}$-HGH from implants was determined over 29 days. Uncoated implants and coated implants with a polymer film at 3, 6, 9 and 12% (by weight) were used. The percentage of HGH released is tabulated (Table 4) and shown in FIG. 6. The release data is the mean determined for 5 implants at each coating level. The results demonstrated that the coating level retards the release of HGH from the implant and that the release rate can be controlled by varying the amount of coating.

TABLE 4

In vitro release of HGH over 29 days
The % release is the mean value for 5 implants

| Uncoated | |
|---|---|
| Time (h) | Release (%) |
| 2.0 | 6.0 |
| 4.0 | 7.1 |
| 6.0 | 8.4 |
| 22.5 | 10.3 |
| 30.0 | 11.8 |
| 47.5 | 13.3 |
| 94.5 | 14.9 |
| 263.0 | 17.3 |
| 433.0 | 20.2 |
| 697.0 | 22.8 |

| Time (h) | % released from implants | | | |
|---|---|---|---|---|
| | 3% coat | 6% | 9% | 12% |
| 6.0 | 5.3 | 0.2 | 0.1 | 0.0 |
| 22.5 | 7.5 | 1.6 | 0.8 | 0.6 |
| 30.0 | 7.9 | 2.3 | 1.2 | 0.9 |
| 47.5 | 8.4 | 3.5 | 2.5 | 2.0 |
| 94.5 | 9.1 | 5.0 | 4.2 | 3.8 |
| 169.5 | 9.9 | 6.3 | 5.5 | 5.2 |
| 221.5 | 10.5 | 7.0 | 6.2 | 5.9 |
| 263.0 | 11.0 | 7.6 | 6.7 | 6.5 |
| 433.0 | 12.1 | 9.0 | 7.9 | 7.7 |
| 697.0 | 13.4 | 10.4 | 9.0 | 8.7 |

EXAMPLE 6

GnRH Implants; In Vivo Release

Using the general method of Example 1 implants were prepared based on a similar formulation to that given in Example 2 except that the peptide used GnRH. The prepared implants had an average weight of 31 mg and were coated with 0, 1.25, 2 or 4% Eudragit E30D. As set-out in Table 5 below, some implants contained 12 or 24 µg of GnRH. Others, both coated and uncoated, contained no GnRH.

Approximately 300 entire Corriedale ewes were monitored for oestrus cycles towards the anoestrus period using harnessed vasectomized rams. When spontaneous cycles were observed in less than 10% of the flock in early November, all ewes underwent endoscopy to assess ovarian activity. 200 anovulatory ewes were selected for the trial. These ewes received progestagen-impregnated sponge pessaries. At sponge removal, 10 days after implantation, groups of 19–20 animals received subcutaneous implants as set out in Table 5. Treatments were administered and observations were made according to the experimental schedule set out in Table 6.

The results are set out in Tables 7 and 8 and the following observations were made. Spontaneous ovulations were observed in 3 of 38 ewes (7.9%) of the pooled control groups. None of these ovulations were accompanied by oestrus.

Ovulations were observed in 20 to 25% of ewes in groups 3, 4 and 5 which received coated cores containing approximately 12 µg GnRH. Oestrus was observed in 100, 80 or 75% of those ewes ovulating in groups 3, 4 and 5 respectively and was typically recorded on the evening of day 2 or the morning of day 3 following implantation (Table 6).

Ovulations were observed in 45% of ewes in group 8 which received implants containing 24 µg GnRH with a 1.25% coating. As the thickness was increased, a greater proportion of the treated ewes were induced to ovulate so that 52.6% ovulated in group 7 (2% coating) and 84.2% ovulated in group 6 (4% coating) of the ewes which ovulated in response to the 24 μg GnRH implants 40–66.7% also showed oestrus with no consistent trend apparent between coating thicknesses.

Uncoated implants containing the low level of GnRH (12 μg GnRH; Group 9) induced only 20% of treated ewes to ovulate and only one of these ovulating ewes also mated. Two of the four ewes which ovulated were observed at endoscopy to have luteinized or vascular follicles which are indicative of dumping of GnRH from the uncoated implants.

Further testing showed that lambs born to ewes treated with implants according to the present invention were normal in appearance, health and behaviour. Thus we concluded that the fertility of anoestrous ewes did not differ between forms of induction of ovulation by means of slow release GnRH.

TABLE 5

| Group | No. | Treatment |
|---|---|---|
| 1 | 19 | Blank implant uncoated |
| 2 | 19 | Blank implant coated 4% |
| 3 | 20 | 12 μg GnRH core coated 4% |
| 4 | 20 | 12 μg GnRH core coated 2% |
| 5 | 20 | 12 μg GnRH core coated 1.25% |
| 6 | 19 | 24 μg GnRH core coated 4% |
| 7 | 19 | 24 μg GnRH core coated 2% |
| 8 | 20 | 24 μg GnRH core coated 1.25% |
| 9 | 20 | 12 μg GnRH core uncoated |

TABLE 6

Protocol and Samples:

| Date | Day | Event |
|---|---|---|
| 7-8/11 | −10 | Whole flock endoscoped to select experimental animals. |
| 8/11 | −10 | Progestagen sponges inserted to trial ewes. |
| 12/11 | −6 | All animals weighed and sponges checked. |
| 18/11 | 0 | Sponges removed. Implants inserted. Change harness colour on rams. |
| 18-22/11 | 0-4 | AM and PM oestrus observations (0700 and 1900 h) |
| 23/11 | 5— | Once daily oestrus observations, continuing. |
| 25/11 | 7 | All 200 ewes bled for progesterone analysis. |
| 28/11 | 10 | All ewes endoscoped (approx. day 8 of expected cycle). |
| 29/11 | 11 | Ewes with ovulations or luteinized follicles bled. |
| 2/12 | 14 | Ewes with ovulations or luteinized follicles bled. |

TABLE 7

Temporal distribution of observed oestrous after treatment with various GnRH formulations.

| | | Group | | | | | | | |
|---|---|---|---|---|---|---|---|---|---|
| | 1 | 2 | 3 | 4 | 5 | 6 | 7 | 8 | 9 |
| | | | | | GnRH (μg) | | | | |
| | 0 | 0 | 12 | 12 | 12 | 24 | 24 | 24 | 12 |
| | | | | | Coating (%) | | | | |
| | 0 | 4 | 4 | 2 | 1.25 | 4 | 2 | 1.25 | 0 |
| DAY 0 AM | | | | | | | | | |
| 18/11 PM | | | | | | | | | |
| DAY 1 AM | | | | | | | | | |
| PM | | | | | | | | | |
| DAY 2 AM | | | | | | | | 3 | |
| PM | | 2 | 2 | 2 | 1 | 3 | 3 | | |
| DAY 3 AM | | 2 | 3 | 1 | 6 | 1 | | | |
| PM | | | 1 | | 2 | | 2 | | |
| DAY 4 AM | 1 | | | | 1 | | | | 1 |
| PM | | | | | | | | | |
| DAYS 5-11 | | | No ewes observed to have mated. | | | | | | |
| MEAN HRS. | 83 | 65.4 | 66 | 59.69 | 72 | 58.5 | 57.2 | 93 | |

TABLE 8

Ovulatory and mating responses in anoestrous Corriedale ewes treated with various GnRH formulations.

| | Group | | | | | | | | |
|---|---|---|---|---|---|---|---|---|---|
| | 1 | 2 | 3 | 4 | 5 | 6 | 7 | 8 | 9 |
| | | | | | GnRH (μg) | | | | |
| | 0 | 0 | 12 | 12 | 12 | 24 | 24 | 24 | 12 |
| | | | | | Coating (%) | | | | |
| | 0 | 4 | 4 | 2 | 1.25 | 4 | 2 | 1.25 | 0 |
| No. in Group | 19 | 19 | 20 | 20 | 20 | 19 | 19 | 20 | 20 |
| OVULATIONS | | | | | | | | | |
| Ewes - ovulating | 2 | 1 | 4 | 5 | 4 | 16 | 10 | 9 | 4 |
| not ovulating | 17 | 18 | 16 | 15 | 16 | 3 | 9 | 11 | 16 |
| % ovulating | 10.5 | 5.3 | 20.0 | 25.0 | 20.0 | 84.2 | 52.6 | 45.0 | 20.0 |
| Cl/ewe ovulating | 1.5 | 1.0 | 1.0 | 1.0 | 1.0 | 1.0 | 1.2 | 1.22 | 1.0 |
| OESTRUS | | | | | | | | | |
| Ewes - mated | 0 | 1 | 5 | 6 | 3 | 10 | 4 | 8 | 1 |
| not mated | 19 | 18 | 15 | 14 | 17 | 9 | 15 | 12 | 19 |
| % Mating | 0 | 5.3 | 25.0 | 30.0 | 15.0 | 52.6 | 21.1 | 40.0 | 5.0 |
| Ovulated & Mated | 0 | 1 | 4 | 4 | 3 | 10 | 4 | 6 | 1 |
| Ovulated & not Mated | 2 | 0 | 0 | 1 | 1 | 6 | 6 | 3 | 3 |
| % Mated/ewes ovulated | 0 | 100 | 100 | 80.0 | 75.0 | 62.5 | 40.0 | 66.7 | 25.0 |
| Mated & not ovulated | 0 | 0 | 1 | 2 | 0 | 0 | 0 | 2 | 0 |
| Not Mated & not ovulated | 17 | 18 | 15 | 13 | 16 | 3 | 9 | 9 | 16 |

EXAMPLE 7

Release of 5H Induced In Vivo by GnRH Implants

In order to test whether or not the GnRH containing implants would induce the release of LH in vivo we devised a model which is extremely sensitive to small amounts of GnRH, viz ovariectomized (Ovx) ewes given sub-cutaneous silastic implants containing oestrogen. Whereas the plasma LH levels in Ovx ewes only slightly elevated after implantation of osmotic mini-pumps releasing GnRH at a rate of 250 ng/h, the response is enhanced with oestrogen treatment. At this release rate, GnRH cannot be measured in peripheral plasma. Thus, to determine whether the GnRH implants would have the same effect on plasma LH levels as osmotic mini-pumps releasing 250 ng/h GnRH, the following experiment was conducted. Ovx oestrogen-treated ewes which were either left untreated or given osmotic mini-pumps (OMP) releasing 250 ng/h GnRH or given implants that were uncoated or coated with 2,4 or 6% Eudragit E30D (% by weight of implant).

The group numbers are given in Table 9. Prior to and during the treatment period jugular venous plasma samples collected at frequent (1-3 h) intervals for LH analysis. After secretory profiles were plotted for each sheep, the area under each curve and the time to reach the peak LH level were determined. These data are presented in Table 9.

The following conclusions were made. The oestrogen-treated spayed ewe provided a sensitive model for evaluation of formulations when anoestrous entire ewes were unavailable. Control implants failed to induce a LH response above baseline levels. It can be seen that the OMP treated sheep gave responses (area under curve) in LH secretion of 190-203 (ng/ml)h in 2 experiments with the time to peak of approx. 8.0 h. Uncoated implants gave much earlier and larger LH responses. Coated implants gave delayed responses and the release patterns were similar to those in the OMP treated sheep, although the total responses were less. The area under the LH curve and the time to reach the LH peak were clearly a function of the amount of Eudragit coating.

TABLE 9

| Group | n | Luteinizing Hormone Response | | |
|---|---|---|---|---|
| | | Mean Area Under Curve (ng/ml)h | Time to Reach Peak (h) | Mean Peak Height (ng/ml) |
| Part I | | | | |
| Control | 5 | 56.8 | | 2.4 |
| O.M.P. | 4 | 190.3 | 8.5 | 13.4 |
| Uncoated | 4 | 337.8 | 3.8 | 67.7 |
| 3.5% Coat | 3 | 61.4 | 6.0 | 11.7 |
| Part II | | | | |
| Control | 3 | 0.0 | | 0.0 |
| O.M.P. | 5 | 202.6 | 8.0 | 31.1 |
| Uncoated | 4 | 390.2 | 4.3 | 106.6 |
| 2% Coat | 5 | 112.0 | 7.8 | 13.1 |
| 4% Coat | 5 | 86.1 | 13.3 | 9.8 |
| 6% Coat | 5 | 26.7 | 19.2 | 2.1 |

EXAMPLE 8

GnRH Release from Implants vs Osmotic Mini-pumps

Osmotic mini-pumps (Alza) provide a reliable way of delivering an active material at a constant rate. Implants and osmotic mini-pumps were compared by loading each with $I^{125}$-GnRH and measuring the release rate in vitro. The mean release profile (n=8) for the mini-pumps and coated implants (n=32) is tabulated (Table 10) and shown in FIG. 7. The release rate of GnRH was similar over a 3-4 day period, during which 30-40% of the total payload was released. The implants used in this study had a 4% coating and were similar to those used in vivo in sheep. Osmotic mini-pumps and implants (4% coat) were shown to produce good ovulation and mating response when implanted in Romney ewes in late anoestrus.

TABLE 10

| In vitro release of GnRH from Implants and Osmotic Mini-Pumps | | |
|---|---|---|
| Time h | Mean % GnRH-$I^{125}$ Implant (n = 32) | Released OMP (n = 8) |
| 2.0 | 0.4 | 0.1 |
| 3.5 | 0.9 | 0.2 |
| 5.0 | 1.5 | 0.3 |
| 8.5 | 2.9 | 1.0 |
| 21.5 | 8.9 | 6.6 |
| 29.0 | 12.2 | 9.4 |
| 45.5 | 18.0 | 16.4 |
| 71.5 | 25.2 | 27.5 |
| 141.5 | 36.8 | 58.1 |
| 166.5 | 41.0 | 69.2 |
| 189.5 | 44.3 | 79.4 |

We claim:

1. A pharmaceutical or veterinary implant for continuous parenteral release of a biologically active peptide or protein by subdermal implantation; said implant comprising a biologically active peptide or protein which exhibits a loss of biological activity in the digestive tract of an animal and an excipient encased within a polymeric coating of an addition polymer substantially free of ionizable groups; said polymeric coating being permeable to said biologically active protein or peptide whereby said coating constitutes a release rate limiting barrier to said biologically active protein or peptide and said polymeric coating being non-rupturing, non-soluble at normal physiological pH and non-degradable over the useful life of the implant; and wherein all of the components of the implant are biocompatible; said implant being made by a process which includes the steps of forming a mixture containing the biologically active peptide or protein and the excipient; forming a pellet from said mixture and applying a coating of a polymer around said pellet to encase said pellet with said polymer; said polymer which is applied to the pellet is a permeable addition polymer substantially free of ionizable groups and at normal physiological pH is non-rupturing, non-soluble and non-degradable over the useful life of the implant, whereby said polymeric coating which encases said pellet constitutes a release rate limiting barrier for said biologically active peptide and biologically active protein.

2. The implant of claim 1 wherein said excipient includes a water soluble component or a water soluble component combined with a water insoluble component.

3. The implant of claim 1 wherein the polymeric coating further includes water soluble material for modifying the permeability of the coating.

4. A pharmaceutical or veterinary implant as claimed in claim 1, characterised in that the excipient consists of water-soluble material.

5. A pharmaceutical or veterinary implant as claimed in claim 1, characterised in that the excipient is a water-insoluble material.

6. A pharmaceutical or veterinary implant as claimed in claim 1, characterised in that the excipient consists of water water soluble and water insoluble materials.

7. A pharmaceutical or veterinary implant as claimed in claim 1, characterised in that the coating is formed an aqueous film forming disperison of a copolymer of ethyl acrylate and methyl methacrylate.

8. A pharmaceutical or veterinary implant as claimed in claim 1, characterised in that the coating is swellable.

9. A pharmaceutical or veterinary implant as claimed in claim 1, characterised in that the molecular weight of the protein or peptide is in the range 1,000 to 50,000.

10. A pharmaceutical implant as claimed in claim 1, characterised in that the protein or peptide influences the reproductive system of a recipient person.

11. A pharmaceutical implant as defined in claim 1, characterised in that the protein or peptide influences the growth of a recipient person.

12. A veterinary implant as claimed in claim 1, characterised in that the protein or peptide influences the reproductive system of a recipient animal.

13. A veterinary implant as defined in claim 1, characterised in that the protein or peptide influences the growth of a recipient animal.

14. A veterinary implant as defined in claim 12, characterised in that the protein or peptide is GnRH.

15. A method for administering a protein or peptide to a human or animal characterised in that an implant as claimed in claim 1, is implanted in the human or animal.

* * * * *